United States Patent
Shine et al.

[11] Patent Number: 6,028,412
[45] Date of Patent: Feb. 22, 2000

[54] DIGITAL FREQUENCY GENERATOR

[76] Inventors: Thomas Adam Shine, 220 Lawrence St., No. 3, Newhaven, Conn. 06511; Ian Basil Shine, 444 Central Park West, New York, N.Y. 10025

[21] Appl. No.: 09/101,011
[22] PCT Filed: Dec. 27, 1996
[86] PCT No.: PCT/GB96/03240
  § 371 Date: Apr. 8, 1998
  § 102(e) Date: Aug. 4, 1998
[87] PCT Pub. No.: WO97/24797
  PCT Pub. Date: Jul. 10, 1997

[30] Foreign Application Priority Data

Dec. 29, 1995 [GB] United Kingdom .................. 9526717

[51] Int. Cl.[7] ....................................................... H02P 8/00
[52] U.S. Cl. ........................................... 318/696; 327/164
[58] Field of Search ..................................... 318/671, 685, 318/696, 606, 607; 307/106; 327/100, 164, 165, 172

[56] References Cited

U.S. PATENT DOCUMENTS

| | | | |
|---|---|---|---|
| 3,701,890 | 10/1972 | Dummermuth | 318/573 |
| 3,805,138 | 4/1974 | Hilker | 318/696 |
| 4,417,189 | 11/1983 | Overfield | 318/696 |
| 4,604,034 | 8/1986 | Wheeldon et al. | 417/18 |
| 4,634,426 | 1/1987 | Kamen | 604/65 |
| 4,661,754 | 4/1987 | Tajima | 318/696 |
| 5,216,346 | 6/1993 | Murakami | 318/696 |
| 5,262,709 | 11/1993 | Yasuda | 318/696 |

Primary Examiner—Robert E. Nappi
Assistant Examiner—Rina I. Duda
Attorney, Agent, or Firm—Burns, Doane, Swecker & Mathis, L.L.P.

[57] ABSTRACT

Generating a clock signal having a desired frequency is accomplished by generating a pulse each time a stored accumulator value is found to be greater than or equal to a stored trigger value The seored accumulator value is incremented by a first iterative value n (r) until the stored accumulator value is greater than or equal to the stored trigger value. Subsequently, the stored accumulator value is decremented by a second iterative value until the stored accumulator value is less than the stored trigger value. During each iteration incrementing the stored accumulator value, a current frequency of the clock spinal is compared to a desired frequency value, and if the two values are different, the first iterative value (r) is corrected by a predetermined rate over one or more subsequent iterations until the frequency of the generator clock signal corresponds to the detected value of the desired frequency.

13 Claims, 17 Drawing Sheets

Fig. 8

TABLE 1

Frequency is an average of the number of pulses shown on each line
m=1000  r=431  desired velocity=431

| time | loops | n | r | pulses | Hz | %error |
|---|---|---|---|---|---|---|
| 0.003 | 3 | 1293 | 431 | 0 | 0.0 | 100.00 |
| 0.007 | 7 | 1017 | 431 | 2 | 500.0 | -16.01 |
| 0.012 | 12 | 1172 | 431 | 4 | 400.0 | 7.19 |
| 0.021 | 21 | 1051 | 431 | 8 | 444.4 | -3.12 |
| 0.040 | 40 | 1240 | 431 | 16 | 421.1 | 2.31 |
| 0.077 | 77 | 1187 | 431 | 32 | 432.4 | -0.33 |
| 0.151 | 151 | 1081 | 431 | 64 | 432.4 | -0.33 |
| 0.300 | 300 | 1300 | 431 | 128 | 429.5 | 0.34 |
| 0.597 | 597 | 1307 | 431 | 256 | 431.0 | 0.01 |
| 1.191 | 1191 | 1321 | 431 | 512 | 431.0 | 0.01 |
| 2.379 | 2379 | 1349 | 431 | 1024 | 431.0 | 0.01 |
| 4.755 | 4755 | 1405 | 431 | 2048 | 431.0 | 0.01 |
| 9.506 | 9506 | 1086 | 431 | 4096 | 431.1 | -0.02 |
| 19.010 | 19010 | 1310 | 431 | 8192 | 431.0 | 0.01 |
| 38.017 | 38017 | 1327 | 431 | 16384 | 431.0 | 0.00 |
| 76.031 | 76031 | 1361 | 431 | 32768 | 431.0 | 0.00 |

Fig. 9

TABLE 2

Frequency is an average of the number of pulses shown on each line
m=10000  r=431  desired velocity=431

| time | loops | n | r | pulses | Hz | %error |
|---|---|---|---|---|---|---|
| 0.002 | 24 | 10344 | 431 | 0 | 0.0 | 100.00 |
| 0.007 | 70 | 10170 | 431 | 2 | 434.8 | -0.88 |
| 0.012 | 117 | 10427 | 431 | 4 | 425.5 | 1.27 |
| 0.021 | 209 | 10079 | 431 | 8 | 434.8 | -0.88 |
| 0.039 | 395 | 10245 | 431 | 16 | 430.1 | 0.21 |
| 0.077 | 766 | 10146 | 431 | 32 | 431.3 | -0.06 |
| 0.151 | 1509 | 10379 | 431 | 64 | 430.7 | 0.07 |
| 0.299 | 2994 | 10414 | 431 | 128 | 431.0 | 0.01 |
| 0.596 | 5963 | 10053 | 431 | 256 | 431.1 | -0.03 |
| 1.190 | 11903 | 10193 | 431 | 512 | 431.0 | 0.01 |
| 2.378 | 23782 | 10042 | 431 | 1024 | 431.0 | -0.00 |
| 4.754 | 47541 | 10171 | 431 | 2048 | 431.0 | 0.00 |

Fig. 10

TABLE 3

Frequency is an average of the number of pulses shown on each line
m=100000  r=431  desired velocity=431

| time | loops | n | r | pulses | Hz | %error |
|---|---|---|---|---|---|---|
| 0.002 | 233 | 100423 | 431 | 0 | 0.0 | 100.00 |
| 0.007 | 697 | 100407 | 431 | 2 | 431.0 | -0.01 |
| 0.012 | 1161 | 100391 | 431 | 4 | 431.0 | -0.01 |
| 0.021 | 2089 | 100359 | 431 | 8 | 431.0 | -0.01 |
| 0.039 | 3945 | 100295 | 431 | 16 | 431.0 | -0.01 |
| 0.077 | 7657 | 100167 | 431 | 32 | 431.0 | -0.01 |
| 0.151 | 15082 | 100342 | 431 | 64 | 431.0 | 0.01 |
| 0.299 | 29931 | 100261 | 431 | 128 | 431.0 | -0.00 |
| 0.596 | 59629 | 100099 | 431 | 256 | 431.0 | -0.00 |
| 1.190 | 119026 | 100206 | 431 | 512 | 431.0 | 0.00 |
| 2.378 | 237820 | 100420 | 431 | 1024 | 431.0 | 0.00 |

Fig. 11

TABLE 4

Frequency is an average at the number of pulses shown on each line
m=100000  r=93  desired velocity=93

| time | loops | n | r | pulses | Hz | % error |
|---|---|---|---|---|---|---|
| 0.011 | 1078 | 100068 | 93 | 0 | 0.0 | 100.00 |
| 0.032 | 3226 | 100018 | 93 | 2 | 93.0 | -0.03 |
| 0.054 | 5377 | 100061 | 93 | 4 | 93.0 | 0.02 |
| 0.097 | 9678 | 100054 | 93 | 8 | 93.0 | -0.00 |
| 0.183 | 18280 | 100040 | 93 | 16 | 93.0 | -0.00 |
| 0.355 | 35484 | 100012 | 93 | 32 | 93.0 | -0.00 |
| 0.699 | 69893 | 100049 | 93 | 64 | 93.0 | 0.00 |

Fig. 12

TABLE 5

Frequency is an average of the number of pulses shown on each line
m=100000   r=939   desired velocity=939

| time  | loops  | n      | r   | pulses | Hz    | % error |
|-------|--------|--------|-----|--------|-------|---------|
| 0.001 | 107    | 100473 | 939 | 0      | 0.0   | 100.00  |
| 0.003 | 320    | 100480 | 939 | 2      | 939.0 | 0.00    |
| 0.005 | 533    | 100487 | 939 | 4      | 939.0 | 0.00    |
| 0.010 | 959    | 100501 | 939 | 8      | 939.0 | 0.00    |
| 0.018 | 1811   | 100529 | 939 | 16     | 939.0 | 0.00    |
| 0.035 | 3515   | 100585 | 939 | 32     | 939.0 | 0.00    |
| 0.069 | 6923   | 100697 | 939 | 64     | 939.0 | 0.00    |
| 0.137 | 13739  | 100921 | 939 | 128    | 939.0 | 0.00    |
| 0.274 | 27370  | 100430 | 939 | 256    | 939.0 | -0.00   |
| 0.546 | 54633  | 100387 | 939 | 512    | 939.0 | -0.00   |
| 1.092 | 109159 | 100301 | 939 | 1024   | 939.0 | -0.00   |

Fig. 13

TABLE 6

Frequency is an average of the number of pulses shown on each line
m=100000   r=9393   desired velocity=9393

| time  | loops  | n      | r    | pulses | Hz     | %error |
|-------|--------|--------|------|--------|--------|--------|
| 0.000 | 11     | 103323 | 9393 | 0      | 0.0    | 100.00 |
| 0.000 | 32     | 100576 | 9393 | 2      | 9523.8 | -1.39  |
| 0.001 | 54     | 107222 | 9393 | 4      | 9090.9 | 3.22   |
| 0.001 | 96     | 101728 | 9393 | 8      | 9523.8 | -1.39  |
| 0.002 | 181    | 100133 | 9393 | 16     | 9411.8 | -0.20  |
| 0.004 | 352    | 106336 | 9393 | 32     | 9356.7 | 0.39   |
| 0.007 | 693    | 109349 | 9393 | 64     | 9384.2 | 0.09   |
| 0.014 | 1374   | 105982 | 9393 | 128    | 9397.9 | -0.05  |
| 0.027 | 2737   | 108641 | 9393 | 256    | 9391.0 | 0.02   |
| 0.055 | 5462   | 104566 | 9393 | 512    | 9394.5 | -0.02  |
| 0.109 | 10913  | 105809 | 9393 | 1024   | 9392.8 | 0.00   |
| 0.218 | 21815  | 108295 | 9393 | 2048   | 9392.8 | 0.00   |
| 0.436 | 43618  | 103874 | 9393 | 4096   | 9393.2 | -0.00  |
| 0.872 | 87225  | 104425 | 9393 | 8192   | 9393.0 | 0.00   |
| 1.744 | 174439 | 105527 | 9393 | 16384  | 9393.0 | 0.00   |

Fig. 14

TABLE 7

Frequency is an average of the number of pulses shown on each line
m=100000   r=93939   desired velocity=93939

| time  | loops  | n      | r     | pulses | Hz       | %error |
|-------|--------|--------|-------|--------|----------|--------|
| 0.000 | 2      | 187878 | 93939 | 0      | 0.0      | 100.00 |
| 0.000 | 4      | 175756 | 93939 | 2      | 100000.0 | -6.45  |
| 0.000 | 6      | 163634 | 93939 | 4      | 100000.0 | -6.45  |
| 0.000 | 10     | 139390 | 93939 | 8      | 100000.0 | -6.45  |
| 0.000 | 19     | 184841 | 93939 | 16     | 88888.9  | 5.38   |
| 0.000 | 36     | 181804 | 93939 | 32     | 94117.6  | -0.19  |
| 0.001 | 70     | 175730 | 93939 | 64     | 94117.6  | -0.19  |
| 0.001 | 138    | 163582 | 93939 | 128    | 94117.6  | -0.19  |
| 0.003 | 274    | 139286 | 93939 | 256    | 94117.6  | -0.19  |
| 0.005 | 547    | 184633 | 93939 | 512    | 93772.9  | 0.18   |
| 0.011 | 1092   | 181388 | 93939 | 1024   | 93945.0  | -0.01  |
| 0.022 | 2182   | 174898 | 93939 | 2048   | 93945.0  | -0.01  |
| 0.044 | 4382   | 161918 | 93939 | 4096   | 93945.0  | -0.01  |
| 0.087 | 8722   | 135958 | 93939 | 8192   | 93945.0  | -0.01  |
| 0.174 | 17443  | 177977 | 93939 | 16384  | 93934.2  | 0.01   |
| 0.349 | 34884  | 168076 | 93939 | 32768  | 93939.6  | -0.00  |
| 0.698 | 69766  | 148274 | 93939 | 65536  | 93939.6  | -0.00  |
| 1.395 | 139530 | 108670 | 93939 | 131072 | 93939.6  | -0.00  |
| 2.791 | 279059 | 123401 | 93939 | 262144 | 93938.9  | 0.00   |

Fig. 15

TABLE 8

Frequency is an average of the number of pulses shown on each line
m=1000000   r=939393   desired velocity=939393

| time  | loops  | n       | r      | pulses | Hz        | %error |
|-------|--------|---------|--------|--------|-----------|--------|
| 0.000 | 2      | 1878786 | 939393 | 0      | 0.0       | 100.00 |
| 0.000 | 4      | 1757572 | 939393 | 2      | 1000000.0 | -6.45  |
| 0.000 | 6      | 1636358 | 939393 | 4      | 1000000.0 | -6.45  |
| 0.000 | 10     | 1393930 | 939393 | 8      | 1000000.0 | -6.45  |
| 0.000 | 19     | 1848487 | 939393 | 16     | 888888.9  | 5.38   |
| 0.000 | 36     | 1818148 | 939393 | 32     | 941176.5  | -0.19  |
| 0.000 | 70     | 1757510 | 939393 | 64     | 941176.5  | -0.19  |
| 0.000 | 138    | 1636234 | 939393 | 128    | 941176.5  | -0.19  |
| 0.000 | 274    | 1393682 | 939393 | 256    | 941176.5  | -0.19  |
| 0.001 | 547    | 1847971 | 939393 | 512    | 937728.9  | 0.18   |
| 0.001 | 1092   | 1817156 | 939393 | 1024   | 939449.5  | -0.01  |
| 0.002 | 2182   | 1755526 | 939393 | 2048   | 939449.5  | -0.01  |
| 0.004 | 4362   | 1632266 | 939393 | 4096   | 939449.5  | -0.01  |
| 0.009 | 8722   | 1385748 | 939393 | 8192   | 939449.5  | -0.01  |
| 0.017 | 17443  | 1832099 | 939393 | 16384  | 939341.8  | 0.01   |
| 0.035 | 34884  | 1785412 | 939393 | 32768  | 939395.7  | -0.00  |
| 0.070 | 69766  | 1692038 | 939393 | 65536  | 939395.7  | -0.00  |
| 0.140 | 139530 | 1505290 | 939393 | 131072 | 939395.7  | -0.00  |

Fig. 16

TABLE 9

Frequency is an average of the number of pulses shown on each line
m=1000000   r=9   desired velocity=939393

| time | loops | n | r | pulses | Hz | %error |
|---|---|---|---|---|---|---|
| 0.111 | 111112 | 1000008 | 9 | 0 | 0.0 | 100.00 |
| 0.198 | 198227 | 1000023 | 29 | 2 | 23.0 | 20.83 |
| 0.244 | 244276 | 1000014 | 49 | 4 | 43.4 | 11.36 |
| 0.300 | 299612 | 1000008 | 89 | 8 | 72.3 | 18.78 |
| 0.361 | 361155 | 1000025 | 169 | 16 | 130.0 | 23.08 |
| 0.426 | 426354 | 1000086 | 929 | 32 | 245.4 | 25.41 |
| 0.494 | 493548 | 1000032 | 649 | 64 | 476.2 | 26.62 |
| 0.562 | 561787 | 1001033 | 1289 | 128 | 937.9 | 27.24 |
| 0.631 | 630559 | 1000761 | 2569 | 256 | 1861.2 | 27.55 |
| 0.700 | 699602 | 1003058 | 5129 | 512 | 3707.8 | 27.71 |
| 0.769 | 768781 | 1010049 | 10249 | 1024 | 7401.1 | 27.79 |
| 0.838 | 838027 | 1004463 | 20489 | 2048 | 14787.9 | 27.83 |
| 0.907 | 907308 | 1012892 | 40969 | 4096 | 29560.8 | 27.85 |
| 0.977 | 976606 | 1027344 | 81929 | 8192 | 59107.0 | 27.86 |
| 1.046 | 1045913 | 1133547 | 163849 | 16384 | 118198.7 | 27.86 |
| 1.115 | 1115223 | 1007707 | 327689 | 32768 | 236387.2 | 27.86 |
| 1.185 | 1184536 | 1062254 | 655369 | 65536 | 472754.0 | 27.86 |
| 1.260 | 1260069 | 1266451 | 939389 | 131072 | 867647.3 | 7.64 |
| 1.400 | 1399597 | 1032483 | 939389 | 262144 | 939395.7 | -0.00 |
| 1.679 | 1678654 | 1503948 | 939389 | 524288 | 939392.3 | -0.00 |
| 2.237 | 2236767 | 1507473 | 939389 | 1048576 | 939394.0 | -0.00 |

Fig. 17

TABLE 10

| time | loops | tank | r (rate) | AccRate | pulse | Hz | %error |
|---|---|---|---|---|---|---|---|
| 0.010 | 200 | 20000 | 100 | 1000 | 0 | 0.0 | 100.00 |
| 5.010 | 100200 | 20000 | 100 | 1000 | 500 | 100.0 | 0.00 |
| 10.010 | 200200 | 20000 | 100 | 1000 | 1000 | 100.0 | 0.00 |
| 15.010 | 300200 | 20000 | 100 | 1000 | 1500 | 100.0 | 0.00 |
| 20.010 | 400200 | 20000 | 100 | 1000 | 2000 | 100.0 | 0.00 |
| 25.010 | 500200 | 20000 | 100 | 1000 | 2500 | 100.0 | 0.00 |
| 31.903 | 638069 | 20990 | 2003 | 1000 | 5000 | 362.7 | 81.89 |
| 33.644 | 672874 | 20105 | 3743 | 1000 | 10000 | 2873.2 | 23.24 |
| 34.801 | 696013 | 20500 | 4900 | 1000 | 15000 | 4321.7 | 11.80 |
| 35.732 | 714649 | 23140 | 5832 | 1000 | 20000 | 5366.0 | 7.99 |
| 36.535 | 730692 | 20362 | 6634 | 1000 | 25000 | 6233.2 | 6.04 |
| 37.250 | 744995 | 23004 | 7349 | 1000 | 30000 | 6991.5 | 4.86 |
| 37.901 | 758024 | 20905 | 8001 | 1000 | 35000 | 7675.2 | 4.07 |
| 38.503 | 770070 | 25593 | 8603 | 1000 | 40000 | 8301.5 | 3.50 |
| 39.068 | 781356 | 23900 | 9000 | 1000 | 45000 | 8860.5 | 1.55 |
| 39.623 | 792467 | 22900 | 9000 | 1000 | 50000 | 9000.1 | -0.00 |
| 40.179 | 803578 | 21900 | 9000 | 1000 | 55000 | 9000.1 | -0.00 |
| 40.734 | 814689 | 20900 | 9000 | 1000 | 60000 | 9000.1 | -0.00 |

DIGITAL FREQUENCY GENERATOR

TECHNICAL FIELD

The present invention relates to a method and apparatus for generating a clock signal. In this application, the term "clock signal" is defined as a series of periodic signals which may be used to clock any particular electronic circuit or device at a fixed or variable frequency. In particular, the clock signal may be used in the generation of any waveform, potentially replacing RC and RL circuits, bistables, sweeping frequency generators, error correcting amplifiers and phase locked loops.

BACKGROUND ART

The generation of a known frequency is common in many commercial applications, including radio equipment, mobile phones, two way radios, television and radio frequency tuners. The need for digital control in such tuners has brought about dedicated phase locked loop integrated circuits which are expensive. These circuits have limitations as they have a predetermined discrete number of frequencies and pre-determined range of frequencies which they can generate. Such an arrangement is commonly seen when tuning a digital car radio where the FM frequency changes in steps of typically 0.1 MHz over a 20 MHz range.

Frequency control is also used in motor controllers, particularly in stepper and DC motor applications where a clock signal controls the speed of the motor. Varying the frequency of the clock signal controls the speed of the rotor. There are many established methods of translating the frequency of a clock signal to drive many different types of electrical motors and many commercially available integrated circuits which perform such translation. Conventional stepper controllers can typically only produce around 250 different predetermined stepping rates so that when the stepping rate needs to be changed it can only be done in a stepwise fashion. Accordingly, it is impossible to obtain a smooth change from one stepping rate to another, which is highly desirable in some applications.

DISCLOSURE OF INVENTION

According to a first aspect of the present invention, a method of generating a clock signal having a desired frequency comprises the step of generating a pulse each time a stored accumulator value is found to be greater than or equal to a stored trigger value, wherein in a first loop the stored accumulator value is iteratively incremented by a first iterative value until the stored accumulator value is greater than or equal to the stored trigger value and subsequently in a second loop the stored accumulator value is decremented by a second iterative value until the stored accumulator value is less than the stored trigger value and, wherein during each iteration of the first loop, a current frequency of the clock signal is compared to a desired frequency value and if the two values are different, the first iterative value is corrected at a predetermined rate over one or more subsequent iterations until the frequency of the generated clock signal corresponds to the detected value of the desired frequency.

Preferably, under conditions where the generated clock signal frequency equals the desired frequency, the first iterative value is set by the value of a detected input corresponding to the desired frequency of the clock signal. An iterative increment equal to the detected value of the desired frequency in Hertz is added to the stored accumulator value during each iteration of the first iterative loop. When the desired frequency of the clock signal changes, the first iterative value is corrected at a predetermined rate over one or more subsequent iterations until the frequency of the generated clock signal, and consequently the first iterative value, corresponds to the detected value of the desired frequency. Accordingly, the frequency of the clock signal is capable of accelerating between two frequencies at a predetermined rate without missing any intermediate frequencies. In the context of a stepper motor, this means that the stepping rate can be accelerated in a manner which approximates very closely to a continuous function.

Preferably, the second iterative value is set by the stored trigger value, whereby the stored trigger value is at least that in Hertz of a pre-determined interrupt frequency at which the first and second iterative loops are driven. More preferably, both the stored trigger value and interrupt frequency are a value $2^n$, where n is a positive integer. This simplifies the comparison between the stored trigger value and the stored accumulator value as the binary value of the stored trigger value is represented by a single bit in a register being set and exceeding the trigger value is also represented by a single bit being set. In this case, an iterative decrement equal to the stored trigger value is subtracted from the stored accumulator value for each iteration of the second iterative loop or if the stored trigger value is $2^n$, then a single bit is cleared in a register. As an alternative, execution of the second loop can be reduced to a single iteration by precalculating the number of pulses that need to be produced. For instance, if the desired frequency is much larger than the stored trigger value then a precalculation can be carried out automatically to determine how many pulses need to be produced for each iteration of the first loop.

Preferably, the number of iterations needed to change the first iterative value is determined by a stored accelerator value which is added to an accelerator-accumulator for each iteration that the first iterative value and the desired frequency are not exactly equal. In such an iteration, each time the accelerator-accumulator is greater than or equal to the stored trigger value, the first iterative value is incremented (or decremented for deceleration) by one and the accelerator-accumulator is reduced by the value of the stored trigger value. Such an arrangement enables the acceleration rate to be controlled accurately in real units (Hertz).

Preferably, the stored trigger value and stored accelerator value are variable. In particular, the stored trigger value may be arranged to be sufficiently large in comparison to an expected desired frequency so that frequencies may be generated which settle very quickly typically within 10 ms. The stored accelerator value may be selected to control the rate at which the first iterative value is corrected when the desired frequency is changed.

According to a second aspect of the present invention, an apparatus for generating a clock signal comprises:

means for detecting an input corresponding to the value of a desired frequency;

means for generating a pulse each time a stored accumulator value is found to be greater than or equal to a stored trigger value;

means for controlling a first loop in which the stored accumulator value is incremented by a first iterative value corresponding to the value of the desired frequency until the stored accumulator value is detected to be greater than or equal to the stored trigger value;

means for controlling a second loop in which the stored accumulator value is decremented by a second iterative value until the stored accumulator value is detected to be less than the stored trigger value; and, means for storing an accelerator value and means for storing an accelerator accumulator value which are used to control a rate of change of the first iterative value when the means for detecting the input value of the desired frequency detects that the value of the desired frequency has changed.

Preferably, the apparatus further comprises a memory for storing the value of the desired frequency, the current frequency, the trigger value, the accumulator value, and the accelerator value. Preferably, the apparatus also comprises means for generating an interrupt signal which controls the speed at which the first and second loops are executed and processing means for carrying out the functions of comparing the value of the stored accumulator value with the stored trigger value, incrementing or decrementing the stored accumulator value and changing the first iterative value at a predetermined rate when the desired frequency changes.

Preferably, the apparatus is implemented on an integrated circuit which comprises a pre-programmed microprocessor.

In one preferred implementation, the clock signal generated by the method and apparatus of the first and second aspects, respectively, of the present invention is used to control a stepper motor to provide continuous acceleration between two stepping rates according to a predetermined velocity profile.

In its simplest form, the present invention can be used to generate a repeated series of pulses at any particular fixed or continuously varying frequency. When coupled with a look-up table or any algorithm which generates a waveform, the method of the invention may be used to generate any desired waveform at any desired frequency. Uses of the present invention include motion control, phase locked loop replacement, harmonic tuning of radio frequencies, frequency generators and any other device which depends upon a fixed or varying frequency. The invention is particularly well suited to governing motor speeds and in particular for controlling stepper motors, including full step, half step and micro-steppers. Similarly, the speed of a DC motor can be regulated with this method by providing the controlling frequency which governs the rotational speed of the armature. As the present invention accurately produces any fixed or changing frequency, it can be used to accelerate and decelerate motors linearly and can be used to perform a series of such motions.

The present invention is very efficient i.e. fast and compact, and can be implemented very cheaply on commercially available integrated circuits and embedded controllers.

BRIEF DESCRIPTION OF DRAWINGS

The present invention will now be described in detail with reference to the accompanying drawings in which:

FIG. 8 presents table 1 which illustrates how the present invention accurately produces frequencies with different interrupt frequency values and settles more quickly at higher interrupt frequencies;

FIG. 9 presents table 2 which illustrates how the present invention accurately produces frequencies with different interrupt frequency values and settles more quickly at higher interrupt frequencies;

FIG. 10 presents table 3 which illustrates how the present invention accurately produces frequencies with different interrupt frequency values and settles more quickly at higher interrupt frequencies;

FIG. 11 presents table 4 which further illustrates how the present invention accurately produces frequencies with different interrupt frequency values and settles more quickly at higher interrupt frequencies;

FIG. 12 presents table 5 which further illustrates how the present invention accurately produces frequencies with different interrupt frequency values and settles more quickly at higher interrupt frequencies;

FIG. 13 presents table 6 which further illustrates how the present invention accurately produces frequencies with different interrupt frequency values and settles more quickly at higher interrupt frequencies;

FIG. 14 presents table 7 which still further illustrates how the present invention accurately produces frequencies with different interrupt frequency values and settles more quickly at higher interrupt frequencies;

FIG. 15 presents table 8 which still further illustrates how the present invention accurately produces frequencies with different interrupt frequency values and settles more quickly at higher interrupt frequencies;

FIG. 16 presents table 9 which illustrates how acceleration from one frequency to another is achieved in accordance with the present invention; and FIG. 17 presents table 10 which illustrates how a clock frequency is automatically changed to achieve a velocity profile in accordance with the present invention.

DETAILED DESCRIPTION

Figure 1:
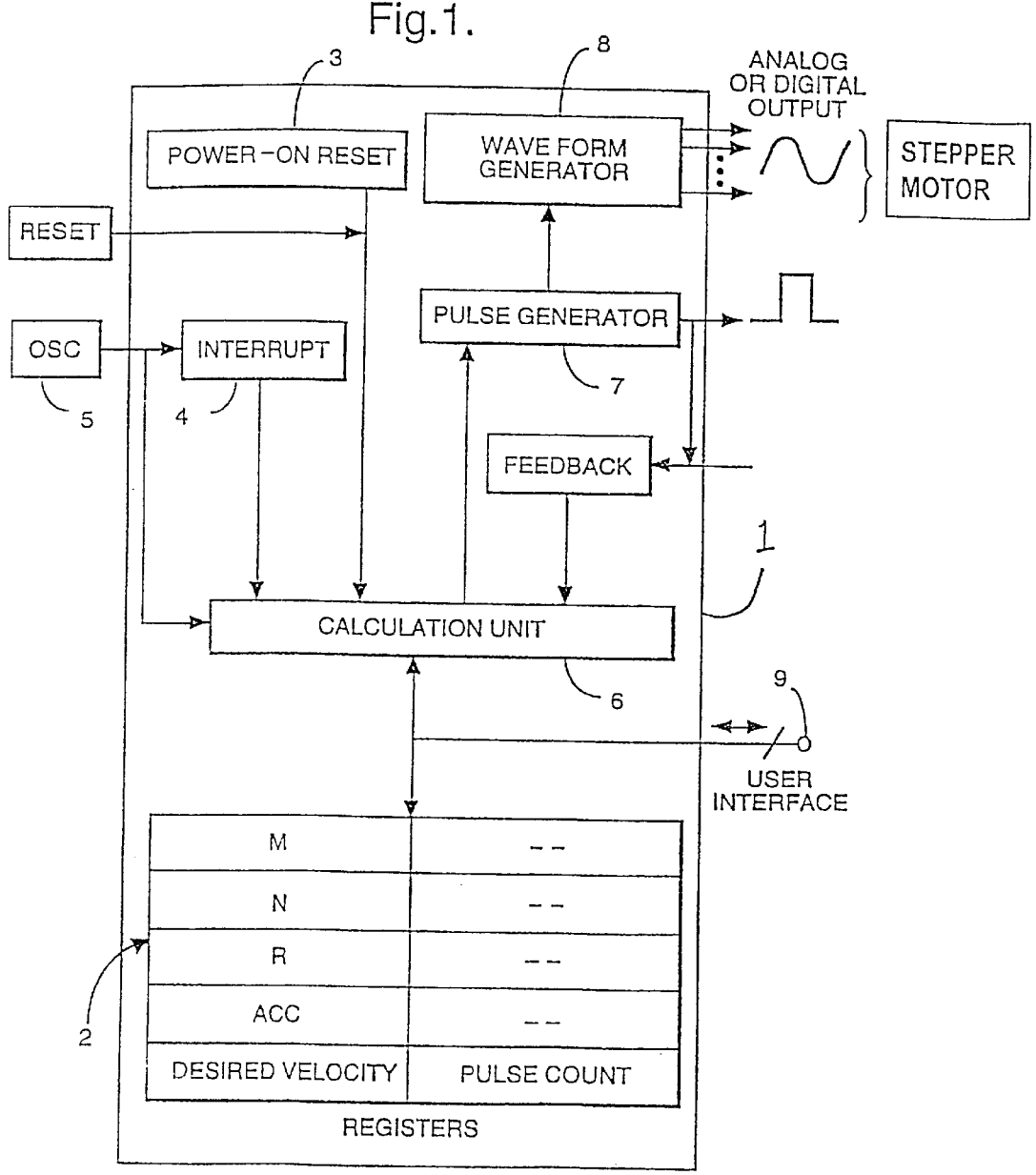
FIG. 1 shows a micro-controller embodying the present invention.

FIG. 1 shows a dedicated pre-programmed microprocessor 1. The microprocessor 1 comprises a number of registers 2 for storing a number of variables, some of which are pre-set when the processor is switched on using the power-on reset 3. The stored variables include a stored trigger value trigger, a stored accumulator value tank, an increment value r, an accelerator value accRate, a desired frequency $F_d$, an accelerator accumulator AccTank and a detected pulse count.

The processor 1 internally generates an interrupt signal using an interrupt generator 4 which is driven by an external oscillator 5, which will be described in detail below.

A pre-programmed unit 6 controls the two loops, described in detail below, which are used to operate a square wave pulse generator 7. In this example, the pulse generator 7 is used to drive a waveform generator 8.

A user interface 9 is provided to control the processor 1 and in particular, change the values of the stored variables in the register 2. Furthermore, a feedback loop may be provided to monitor the output of the pulse generator 7.

Figure 2:
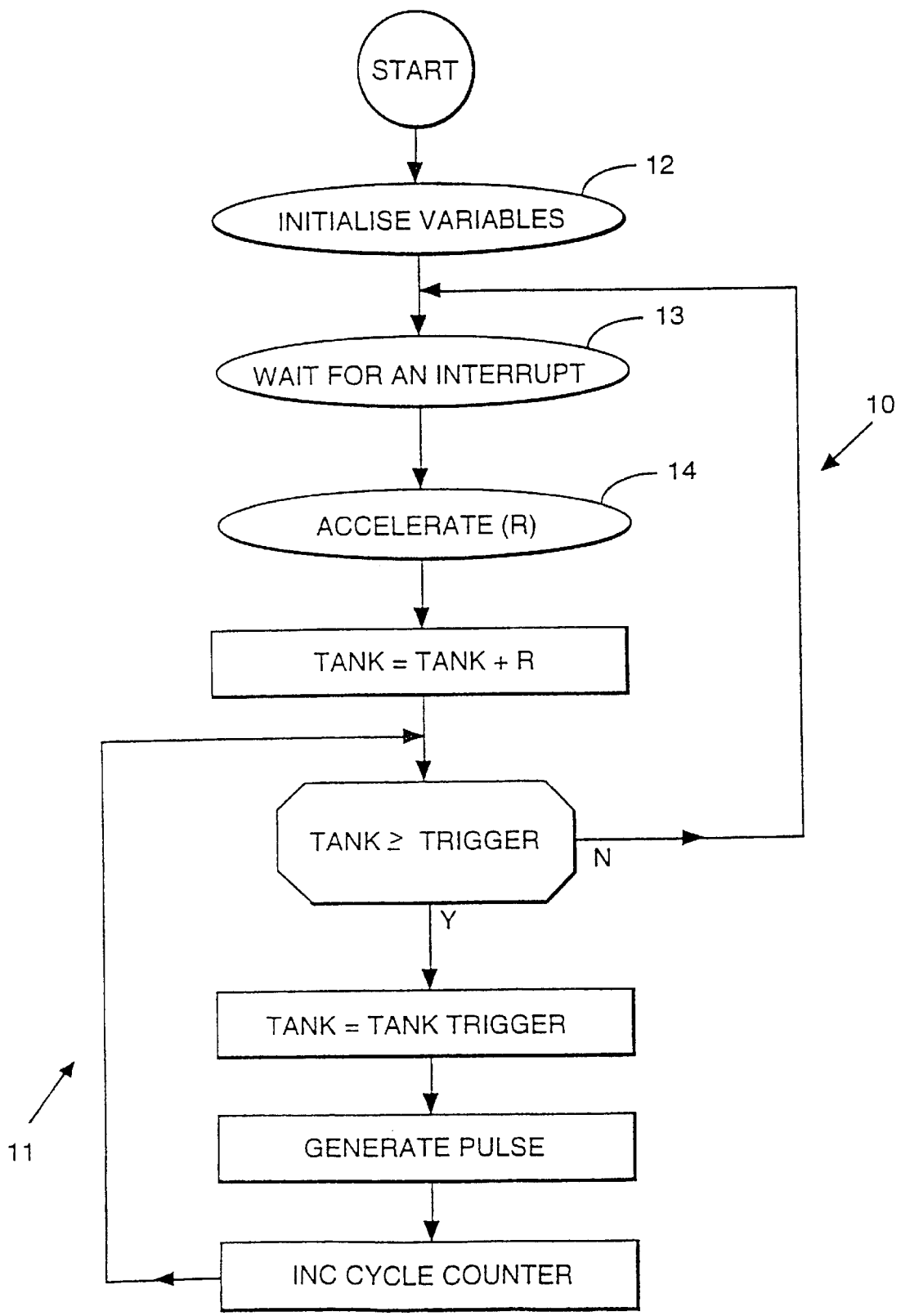
FIG. 2 is a flow diagram illustrating the method of the present invention.

FIG. 2 shows a flow diagram of the process carried out by the processor 1 when generating a clock signal having a desired frequency.

When the pre-programmed processor 1 is first switched on, the program initializes the variables trigger, tank AccTank, accRate and r.

Thereafter, in a first loop 10, each time an interrupt signal is generated by the interrupt generator 4, the processor 1 checks to see if the user has entered a desired frequency and if so, stores this value as the desired frequency. In this example, the processor 1 is preprogrammed to initialise the variable r, termed the iterative increment, as zero and so this iterative increment is increased over a number of iterations in an acceleration routine which is described in detail below with respect to FIG. 5 of the drawings until the iterative increment equals the detected desired frequency. As an alternative, upon initialisation, the processor 1 can instead wait until a desired frequency is detected and there after preset the iterative increment r to equal the desired frequency, so that no initial acceleration of the iterative increment r is required.

The processor 1 subsequently increases the tank value by a value equal to iterative increment r. The processor then compares the tank value and trigger value and if the tank value is found to be greater than or equal to the trigger value then in a second loop 11, the processor decrements the present value of the tank value by the value of the trigger value and a clock pulse is generated. The pulse counter is incremented by 1 and the comparison of the trigger value and tank value is made again. In this example, if necessary, the second loop 11 is repeated until the tank value is found to be less than the trigger value. Once the tank value is found to be less than the trigger value, the first loop 10 starts again, whereby the tank value is iteratively incremented over one or more cycles of the first loop 10 until the conditioned that tank is greater than or equal to trigger is again satisfied.

Figure 3:
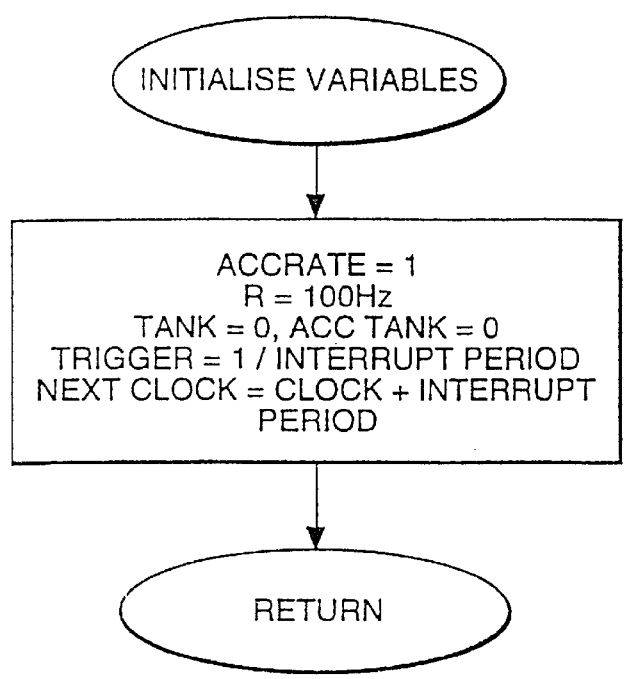
FIGS. 3 to 5 show in an expanded form individual steps in the method of the present invention shown in FIG. 2.

Turning to each box of the flow diagram in FIG. 2 in more detail, the "initialise variables" box 12 is shown in more detail in FIG. 3. In this example, upon initialisation, the processor 1 sets the accelerator value accRate to be 1 Hz s$^{-2}$, the iterative increment value r to be 100 Hz, the tank value and AccTank value to zero and the value trigger to the frequency of the interrupt signal.

Figure 4:
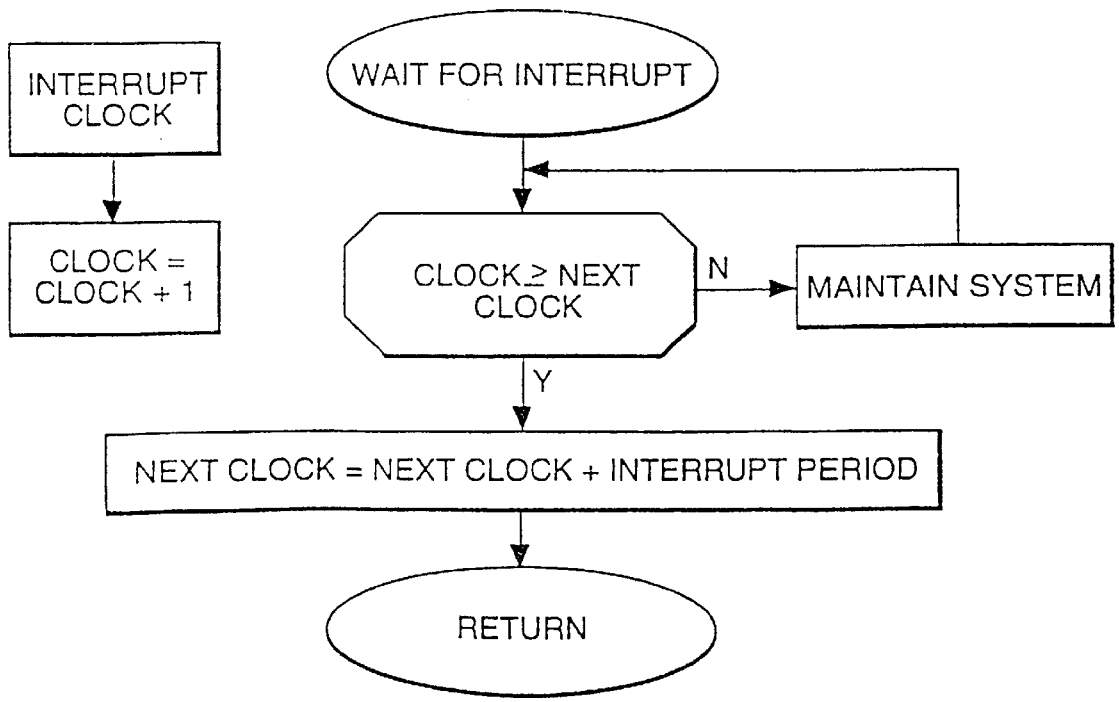

The operation of the "wait for an interrupt" box 13 is illustrated in the flow diagram of FIG. 4. The entire system is operated at the speed of the interrupt signal which is driven by the external oscillator 5. The system is maintained between interrupts and it is during this period that the user can input signals via the user interface 9 to change variables. The frequency of the interrupt signal can be preset to any value including that of the oscillator 5 enabling frequency synthesis equal to that of the oscillator 5 as every iteration can be executed simultaneously, or effectively so, through the use of pipelines or equivalent standard techniques.

Figure 5:
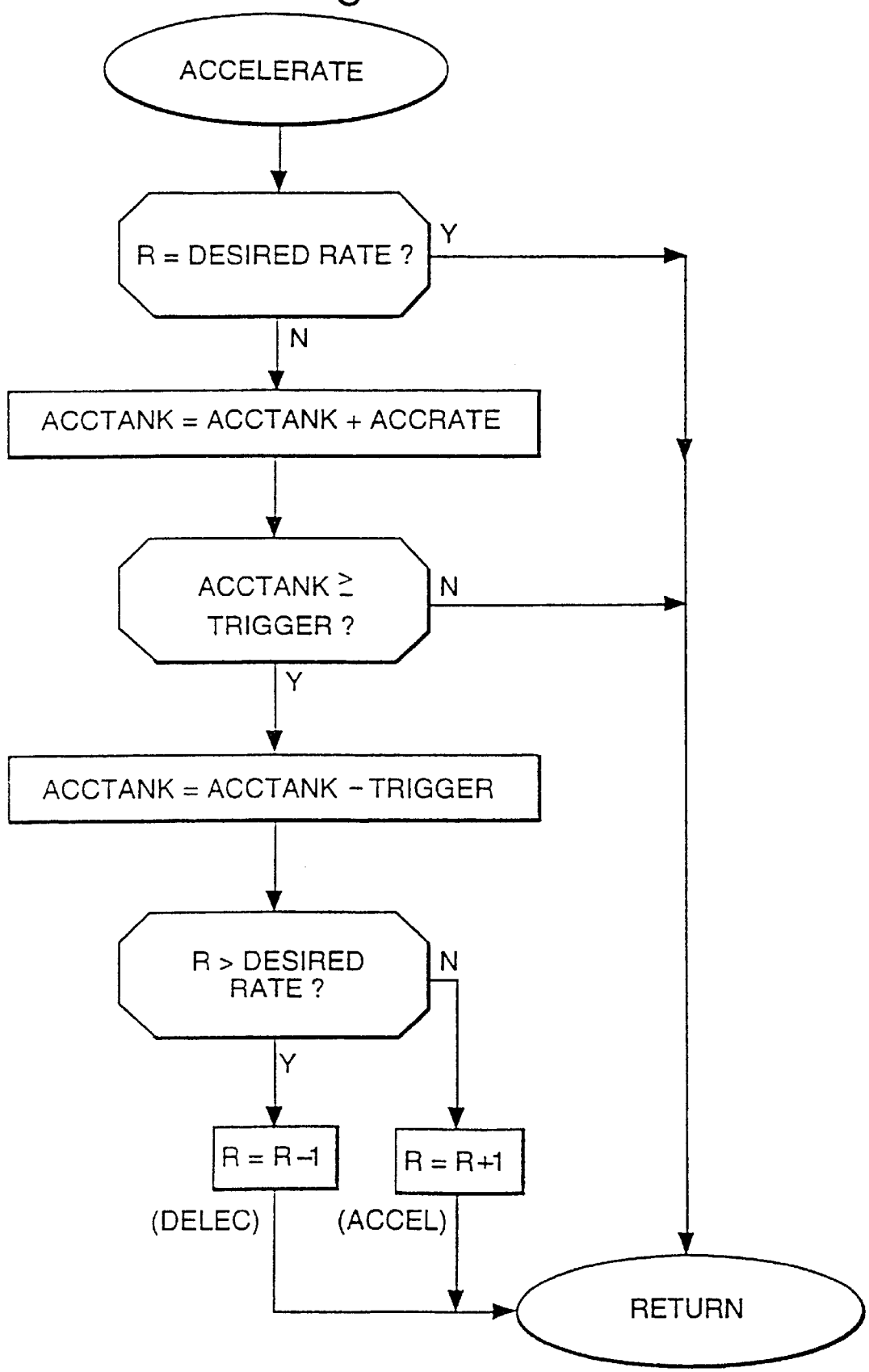

FIG. 5 shows the operation of the "accelerate (r)" box 14. When processor 1 detects that the stored value of the desired frequency is different to the current iterative increment value of r of the first loop 10, the accelerator value accRate is added to an accelerator-accumulator AccTank. AccTank is subsequently compared to the trigger value and if it is greater than or equal to the trigger, AccTank is decremented by the value of trigger and r is incremented (or decremented for deceleration) by one.

During subsequent cycles of the first loop these steps are repeated until r equals the desired frequency. In this manner, the process can accelerate from one frequency to another at a precisely controlled rate set by the accelerator value accRate.

In essence, the present invention depends upon an input frequency, used typically as an interrupt, and three variables, namely, trigger, r and tank. The variable trigger is set to the interrupt frequency in Hertz and is usually never changed, the value r is set to the desired frequency in Hertz which can be altered at any time and tank is an accumulator value. Each time there is an interrupt the increment value r is adjusted if the desired frequency is not yet achieved, tank is incremented by the value of r and tank is compared to trigger. If tank is greater than or equal to trigger a pulse is generated and additional action may be taken such as taking a step on the stepper motor, altering the waveform of a pulse width modulator or altering some other value or physical setting. Furthermore, internal registers 2 can be used to maintain cycle counts, step counts, current frequency, actual frequency, and flags indicating if the frequency is changing and other such information.

Each time tank is found to be greater than or equal to trigger, tank is assigned the value of tank-triqger, which is always positive or zero and a pulse is produced. Likewise, as the value of tank is never cleared, only decreased by trigger, tank always maintains a remainder and will minimise the actual error of frequency generated to less than one period of the interrupt frequency.

The error of the frequency generated is non-accumulating. If the desired frequency is less than or equal to the interrupt frequency then the error is never more than 1 interrupt clock period. If the desired frequency is greater than the interrupt clock frequency, the process is said to be saturated and bunches pulses before the next interrupt so as to maintain the correct number of pulses each interrupt. While the average frequency will be maintained, there may be systems where such a technique is unacceptable. Other techniques, such as producing two or more equally spaced pulses each time a system generates a pulse, hardware frequency doublers, or hardware generated delays, may be used in conjunction with this method. For example, the second loop can be reduced to a single iterative step for cases where the desired frequency exceeds the trigger value by precalculating the number of pulses required following each iteration of the first loop. However, for most systems these techniques are not needed as in practice it is easy to choose interrupt clock frequencies which are higher than the maximum frequency desired.

In applications where the interrupts may themselves be interrupted or entirely missed, the process will maintain a correct frequency provided that the accumulator value is incremented by the iterative increment for each interrupt that is missed or abbreviated. When the system has time to completely service the interrupt, pulse bunching corrects any temporary quiescent errors. The number of missed interrupts can be recorded separately, can be calculated from a comparison with a real time clock or the entire process can be dependent upon comparison with a real time clock instead of an interrupt.

When this system is used with stepper motors, and particularly with micro-steppers, saturation has no measurable effect on the motor. This is because pulse bunching occurs at frequencies which are much higher than motors can respond to. Typically, a stepper motor rotor cannot respond to a change in coil voltage in less than 20 milliseconds due to the rotors inertia and the reluctance of the copper windings. As in practice even on relatively slow, low cost integrated circuits saturation only occurs at frequencies above approximately 10 KHz, the effect on the motor is invisible. Moreover, when used with micro-steppers or look-up tables, instead of bunching pulses together and rapidly sending a sequential set of values to a motor coil, only the last value in the set needs to be sent, as the intermediate values have no effect on the motor. This skipping technique allows for very high frequencies to control a micro-stepper, without loss of position step count or accuracy. The transition from normal operation to saturation is automatically performed by the process whenever the frequency exceeds a system dependent limit. The transition is smooth as pulse bunching is used only to maintain the correct average frequency and the uses of pulse bunching is always minimised.

One advantage of the present invention is that the variables can be altered while the system is running. By varying the value r either directly or indirectly through the accelerate loop, the method of the present invention will accelerate, maintain and decelerate to any frequency up to the implementation dependent maximum and such information as position or frequency can be reported in real time. The rate of acceleration and deceleration can be controlled by altering the value accRate which in turn may alter r at each interrupt. Further, different rates for acceleration and deceleration can be achieved through the use of separate variables.

Due to the very simple and compact nature of the process, and its dependence only on a comparison feature and either addition and subtraction or with a suitable interrupt frequency, a bitset and bitclear feature, the present invention can be implemented by the cheapest and least computationally powerful micro-controllers resulting in very low cost devices. Low cost embedded controllers employing this method to control a stepper motor at rates up to 15,625 steps per second can be achieved without skipping any frequencies and can be configured to produce rates up to 31,000 steps per second while skipping every other frequency. When used with more powerful processors or programmable logic devices, the maximum error-free frequency increases up to a limit of the device's oscillator frequency. If such a process is made into dedicated silicon, a non-skipping, non-saturation frequency of 15 MHz can be achieved and frequencies as high as 300 MHz are currently possible. The limitation upon frequency is entirely silicon based as every iteration can be executed concurrently in a single clock cycle. This frequency maximum is continually increasing and by using more exotic materials, such as GaAs, this method could currently generate frequencies in excess of 1 GHz. When this method is used with a micro-controller all that is typically needed to control a stepper-motor is a source clock and power amplifier as the signals needed for full, half or micro-stepping can be generated internally with existing micro-controllers.

The process can produce fractional frequencies by altering the value of trigger or by performing an equivalent operation. For example, frequencies with a 0.1 Hz resolution are produced if triccer is set to ten times the interrupt frequency instead of the interrupt frequency and r is set to ten times the desired rate. Similarly, this routine can be used with floating-point numbers instead of integers, to produce fractional frequencies.

This method can also be used as part of a closed loop system, where a position-encoder mounted on the motor provides information about the motors position. Such a system is used to verify that the actual position is in accordance with the internally calculated position, and minimizes any difference.

One major distinguishing feature of the present invention is that in contrast to existing frequency generators, the clock signal frequencies generated in the present invention are independent of the input clock frequency. Further, the method has the capability to accurately generate every frequency from 0 to a system dependent maximum and likewise generate a linear acceleration rate from 0 to a system dependent maximum.

Tables 1 to 9 (FIGS. 8–16) illustrate how the method accurately produces frequencies with different interrupt frequency values and settles more quickly at higher interrupt frequencies. Furthermore, Table 9 shows how the method accelerates from one frequency to another.

Figure 6:
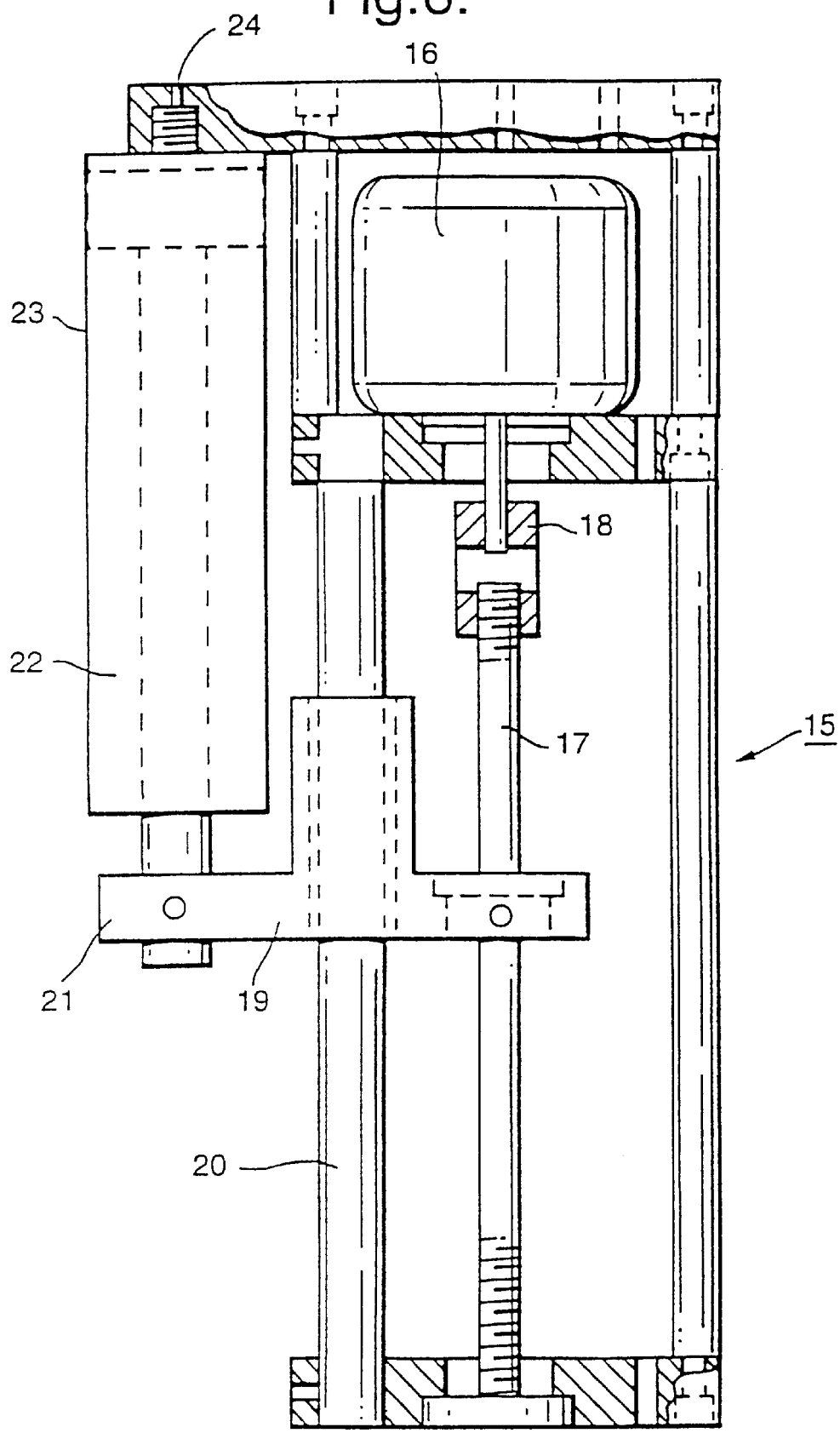
FIG. 6 shows a fluid delivery apparatus which includes a stepper motor used to drive a syringe piston.

An example of an implementation of the present invention is shown in FIG. 6. A fluid delivery apparatus 15 comprises a stepper motor 16 controlled using the frequency generator of the present invention (not shown). The stepper motor 16 rotates a lead-screw 17 via a coupling 18 to drive a member 19 up and down a vertical cylindrical post 20. One arm 21 of the member 19 is connected to a piston 22 of a syringe 23 which has an inlet/outlet 24 at its upper end.

In use, as the syringe piston 22 is returned to its lower position (not shown) a dilutent is allowed to fill the syringe 23. Operating the motor 16 in the opposite direction at a desired stepping rate drives the lead-screw assembly and returns the syringe piston 22 upwardly, discharging the fluid through the outlet 24 at a controlled velocity.

A digital diluter comprises two such fluid delivery assemblies 15 and the purpose is to mix the contents of the two syringes at a predetermined rate to achieve a change in concentration of the mixture i.e. a concentration gradient. Conventional stepper motor controllers are limited as they can only generate a predetermined discrete number of frequencies over a predetermined range. Accordingly, the velocity of each syringe piston can only be changed in a rather coarse stepwise fashion which only approximates to a linear velocity profile. Each time the velocity of the syringe piston steps up or down the flow of fluid from the syringe is disturbed thus reducing the accuracy of any measurements made with respect to the mixture.

Figure 7A:
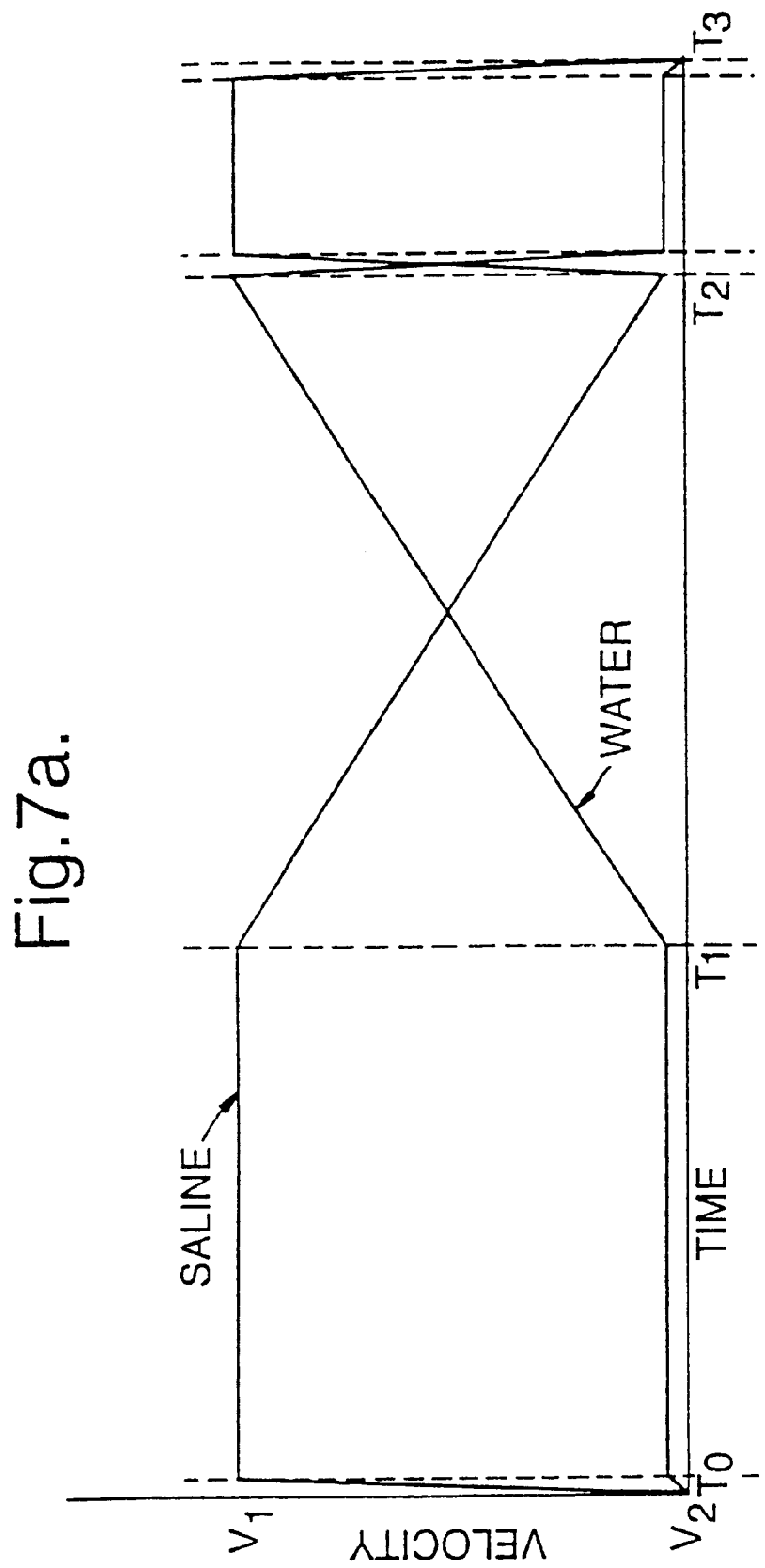
FIG. 7a shows a graph of the velocity of fluids discharged from two separate syringes, each syringe driven by the apparatus shown in FIG. 6 and controlled by the frequency generator of the present invention.
Figure 7B:
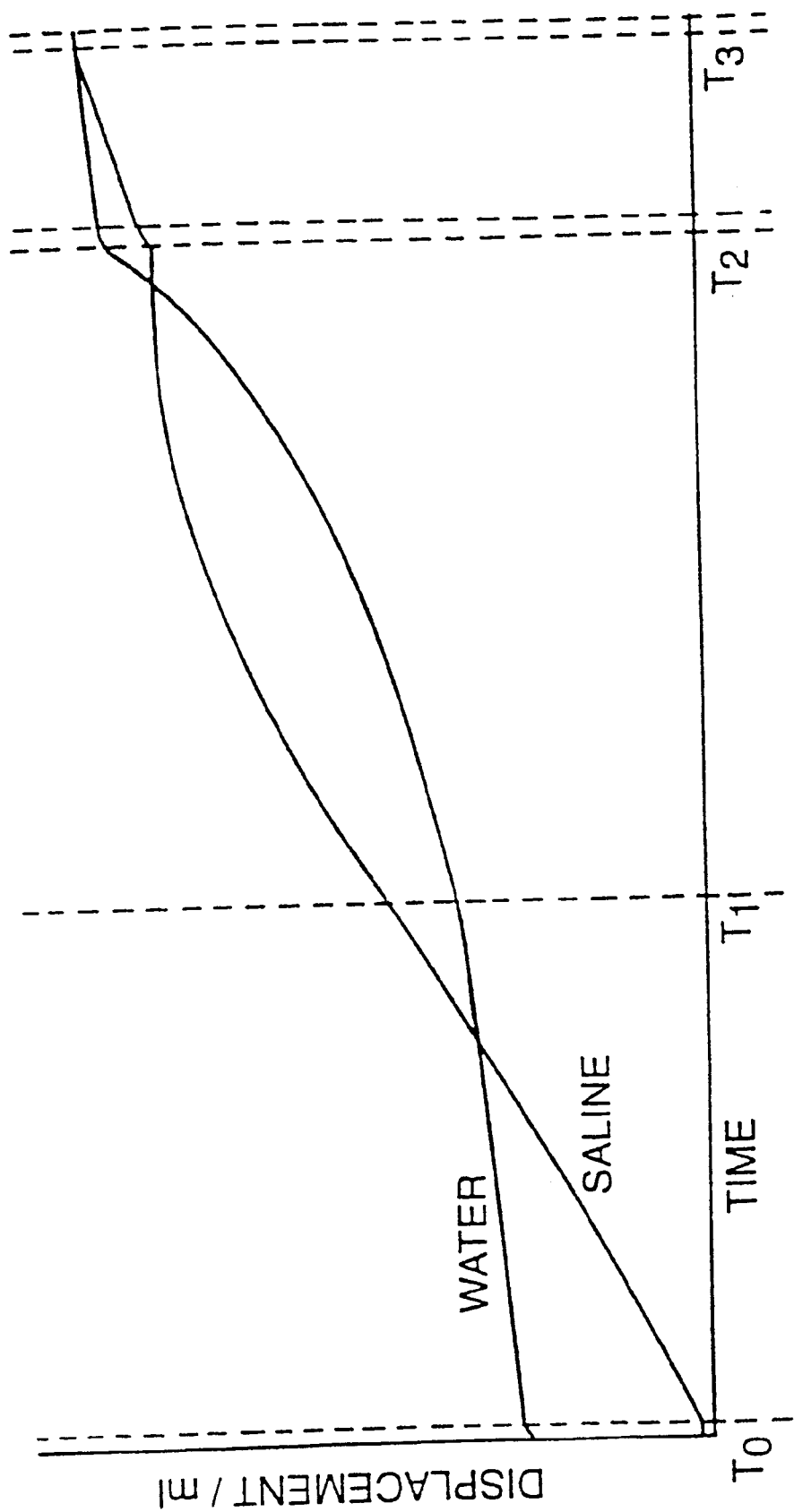
FIG. 7b shows a graph of syringe piston displacement for the two separate syringes driven by the apparatus shown in FIG. 6.

In contrast, the frequency generator of the present invention is capable of accelerating a stepper motor between two stepping rates according to a predetermined velocity profile. FIGS. 7a and 7b show, respectively, graphs of velocity against time for fluid discharged from two syringes and the relative displacement of the pistons of the two syringes.

In this example, a saline sample is to be mixed with a sample of pure water. As shown in FIG. 7a, the stepper motor driving the syringe filled with saline solution accelerates the syringe piston to discharge fluid at a velocity $V_1$, whilst the stepper motor driving the syringe filled with pure water accelerates the syringe piston to discharge fluid at a lower velocity $V_2$.

Once a constant flow rate from each syringe has been established, at time $T_1$ the stepper controller associated with the saline filled syringe decelerates linearly over a period $T_2$-$T_1$ to a velocity $V_2$ whilst simultaneously, the stepper controller associated with the water filled syringe accelerates linearly to velocity $V_1$. During this period, the combined flow rate of the two syringes remains constant. Finally, the two syringes are flushed over the period $T_3$-$T_2$.

As illustrated by this example, the frequency generator of the present invention can accelerate between any two frequencies in a linear rather than stepwise fashion at a rate determined by the user. In practice, the user pre-programs the system to change frequency after a predetermined period or number of pulses rather than entering a new desired frequency manually. The rate of change of velocity for a given displacement is determined by the variable accurate (see FIG. 5).

Table 10 (FIG. 17) shows an example of how a preprogrammed microprocessor can automatically change a clock signal frequency to achieve the type of velocity profile shown in FIG. 7a. In this example, the frequency remains constant for the first 3000 clock pulses at 100 Hz whereupon the desired frequency changes to 9 KHz and the rate, r, or first iterative increment, accelerates from 100 Hz to 9 KHz over a period of around 20 seconds or 42000 pulses.

We claim:

1. A method of generating a clock signal having a desired frequency comprising the step of generating a pulse each time a stored accumulator value is found to be greater than or equal to a stored trigger value, wherein in a first loop the stored accumulator value is iteratively incremented by a first iterative value until the stored accumulator value is greater than or equal to the stored trigger value and subsequently in a second loop the stored accumulator value is decremented by a second iterative value until the stored accumulator value is less than the stored trigger value, and wherein during each iteration of the first loop, a current frequency of the clock signal is compared to a desired frequency value and if the two values are different, the first iterative value is corrected at a predetermined rate over one or more subsequent iterations until the frequency of the generated clock signal corresponds to the detected value of the desired frequency.

2. A method according to claim 1, in which under conditions where the generated clock signal frequency equals the desired frequency, the first iterative value is set by the value of a detected input corresponding to the desired frequency of the clock signal.

3. A method according to claim 1, in which the second iterative value is set by the stored trigger value, whereby the stored trigger value is at least that in Hertz of a predetermined interrupt frequency at which the first and second iterative loops are driven.

4. A method according to claim 1, in which both the stored trigger value and interrupt frequency are a value $2^n$, where n is a positive integer.

5. A method according to claim 1, in which the number of iterations needed to change the first iterative value is determined by a stored accelerator value which is added to an accelerator-accumulator for each iteration that the first iterative value and the desired frequency are not exactly equal.

6. A method according to claim 5, in which the stored trigger value and stored accelerator value are variable.

7. A method of controlling a stepper motor comprising the steps of:
generating a clock signal having a desired frequency; and
providing continuous acceleration between two stepping rates according to a predetermined velocity profile using the generated clock signal, wherein said step of generating the clock signal having the desired frequency comprises the steps of generating a pulse each time a stored accumulator value is found to be greater than or equal to a stored trigger value, wherein in a first loop the stored accumulator value is iteratively incremented by a first iterative value until the stored accumulator value is greater than or equal to the stored trigger value and subsequently in a second loop the stored accumulator value is decremented by a second iterative value until the stored accumulator value is less than the stored trigger value, and wherein during each iteration of the first loop, a current frequency of the clock signal is compared to a desired frequency value and if the two values are different, the first iterative value is corrected at a predetermined rate over one or more subsequent iterations until the frequency of the generated clock signal corresponds to the detected value of the desired frequency.

8. An apparatus for generating a clock signal comprising:
means for detecting an input corresponding to the value of a desired frequency; means for generating a pulse each time a stored accumulator value is found to be greater than or equal to a stored trigger value; means for controlling a first loop in which the stored accumulator value is incremented by a first iterative value corresponding to the value of the desired frequency until the stored accumulator value is detected to be greater than or equal to the stored trigger value; means for controlling a second loop in which the stored accumulator value is decremented by a second iterative value until the stored accumulator value is detected to be less than the stored trigger value; and, means for storing an accelerator value and means for storing an accelerator accumulator value which are used to control a rate of change of the first iterative value when the means for detecting the input value of the desired frequency detects that the value of the desired frequency has changed.

9. An apparatus according to claim 8, further comprising a memory for storing the value of the desired frequency, the current frequency, the trigger value, the accumulator value, and the accelerator value.

10. An apparatus according to claim 8, further comprising means for generating an interrupt signal which controls the speed at which the first and second loops are executed and processing means for carrying out the functions of comparing the value of the stored accumulator value with the stored trigger value, incrementing or decrementing the stored accumulator value and changing the first iterative value at a predetermined rate when the desired frequency changes.

11. An apparatus according to claim 8, implemented on an integrated circuit which comprises a preprogrammed microprocessor.

12. A drive system comprising:
an apparatus for generating a clock signal, wherein said apparatus includes means for detecting an input corresponding to the value of a desired frequency; means for generating a pulse each time a stored accumulator value is found to be greater than or equal to a stored trigger value; means for controlling a first loop in which the stored accumulator value is incremented by a first iterative value corresponding to the value of the desired frequency until the stored accumulator value is detected to be greater than or equal to the stored trigger value; means for controlling a second loop in which the stored accumulator value is decremented by a second iterative value until the stored accumulator value is detected to be less than the stored trigger value; and, means for storing an accelerator value and means for storing an accelerator accumulator value which are used to control a rate of change of the first iterative value when the means for detecting the input value of the desired frequency detects that the value of the desired frequency has changed; and
a stepper motor, wherein the stepper motor is driven by the clock signal generated by the clock generator apparatus.

13. A fluid delivery apparatus comprising a plurality of delivery syringes, each delivery syringe comprising a syringe housing defining a tubular passage having a fluid outlet, and a syringe plunger arranged to slide axially within the tubular passage and seal one end of the tubular passage, the fluid delivery apparatus further comprising syringe plunger drive means arranged to drive the syringe plunger along at least part of the length of the tubular passage according to a predetermined velocity profile for the delivery syringe and discharge fluid through the fluid outlet, wherein the predetermined velocity profile of each delivery syringe is such that, in use, a combined flow rate of fluid discharged simultaneously from the outlets of the plurality of delivery syringes is maintained substantially constant over at least a portion of the range of movement of the plurality of plungers, and wherein the syringe plunger drive means comprises;

an apparatus for generating a clock signal, wherein said apparatus includes means for detecting an input corresponding to the value of a desired frequency; means for generating a pulse each time a stored accumulator value is found to be greater than or equal to a stored trigger value; means for controlling a first loop in which the stored accumulator value is incremented by a first iterative value corresponding to the value of the desired frequency until the stored accumulator value is detected to be greater than or equal to the stored trigger value; means for controlling a second loop in which the stored accumulator value is decremented by a second iterative value until the stored accumulator value is detected to be less than the stored trigger value; and, means for storing an accelerator value and means for storing an accelerator accumulator value which are used to control a rate of change of the first iterative value when the means for detecting the input value of the desired frequency detects that the value of the desired frequency has changed; and a stepper motor, wherein the stepper motor is driven by the clock signal generated by the clock generator apparatus.

* * * * *